US00PP27840P2

(12) United States Plant Patent
Pineau

(10) Patent No.: US PP27,840 P2
(45) Date of Patent: Apr. 4, 2017

(54) ***HIBISCUS SYRIACUS* PLANT NAMED 'MINDOUB1'**

(50) Latin Name: *Hibiscus syriacus*
Varietal Denomination: MINDOUB1

(71) Applicant: Patrick Pineau, Saint Mathurin sur Loire (FR)

(72) Inventor: Patrick Pineau, Saint Mathurin sur Loire (FR)

(73) Assignee: Pepinieres Minier SA, Beaufort en Vallee (FR)

( * ) Notice: Subject to any disclaimer, the term of this patent is extended or adjusted under 35 U.S.C. 154(b) by 0 days.

(21) Appl. No.: 14/756,518

(22) Filed: Sep. 14, 2015

(51) Int. Cl.
*A01H 5/02* (2006.01)

(52) U.S. Cl.
USPC ..... Plt./257

(58) Field of Classification Search
USPC ..... Plt./257
See application file for complete search history.

(56) References Cited

PUBLICATIONS

PLUTO Plant Variety Database Aug. 10, 2016 . p. 1.*

* cited by examiner

*Primary Examiner* — Annette Para
(74) *Attorney, Agent, or Firm* — Penny J. Aguirre

(57) ABSTRACT

A new cultivar of *Hibiscus* named 'MINDOUB1', characterized by its medium sized double flowers that are white in color with a pink-purple flush with occasional irregular markings of pink-purple, its sterile flowers, its upright pant habit, and its vigorous growth habit.

2 Drawing Sheets

Botanical classification: *Hibiscus syriacus.*
Cultivar designation: 'MINDOUB1'.

BACKGROUND OF THE INVENTION

The present invention relates to a new and distinct cultivar of *Hibiscus* plant, botanically known as *Hibiscus syriacus* 'MINDOUB1', and will be referred to hereafter by its cultivar name, 'MINDOUB1'. 'MINDOUB1' is a new cultivar of Rose of Sharon, a deciduous shrub grown for use as a landscape plant.

The new cultivar was developed through an on-going breeding program conducted by the Inventor in La Menitre, France. The objectives of the breeding program are to develop new cultivars of *Hibiscus* that exhibit large double flowers.

The Inventor made a cross in July of 2004 between *Hibiscus syriacus* 'Notwoodtwo' (U.S. Plant Pat. No. 12,612) as the female parent and *Hibiscus syriacus* 'Leopoldii' (not patented) as the male parent. 'MINDOUB1' was selected as a single unique plant in 2007 from the resulting seedlings from the above cross.

Asexual propagation of the new cultivar was first accomplished by grafting in La Menitre, France in 2008 by the Inventor. Asexual propagation by grafting has determined that the characteristics of the new cultivar are stable and are reproduced true to type in successive generations.

SUMMARY OF THE INVENTION

The following traits have been repeatedly observed and represent the characteristics 'MINDOUB1'. These attributes in combination distinguish 'MINDOUB1' as a new and distinct cultivar of *Hibiscus.*

1. 'MINDOUB1' exhibits medium sized double flowers that are white in color with a pink-purple flush with occasional irregular markings of pink-purple.
2. 'MINDOUB1' exhibits sterile flowers.
3. 'MINDOUB1' exhibits an upright pant habit.
4. 'MINDOUB1' exhibits a vigorous growth habit.

'MINDOUB1' can be most closely compared to its parent plants. The female parent of 'MINDOUB1', 'Notwoodtwo', differs from 'MINDOUB1' in having larger semi-double flowers that are white in color (without any pink flush) and fertile. The male parent of 'MINDOUB1', 'Leopoldii', differs from 'MINDOUB1' in having a smaller plant stature, smaller flowers and flower buds, flowers with petaloid stamens that are fewer, smaller and white flushed with red-pink.

BRIEF DESCRIPTION OF THE DRAWINGS

The accompanying colored photograph illustrates the overall appearance and distinct characteristics of the new *Hibiscus*. The photographs in FIG. 1 and FIG. 2 were taken of a three year-old plant of 'MINDOUB1' as grown in a trial pot in LA MENITRE, France.

The photograph in FIG. 1 provides a side view of 'MINDOUB1' in bloom.

Figure 1:
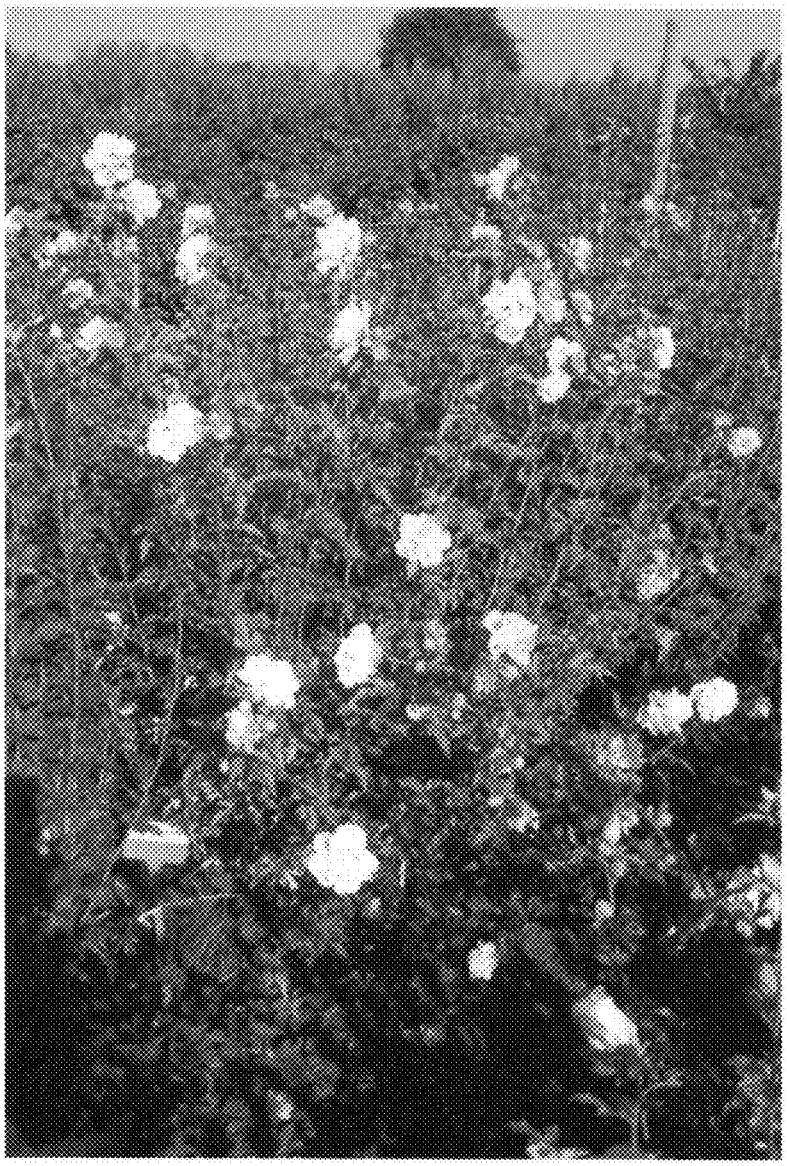
Figure 2:
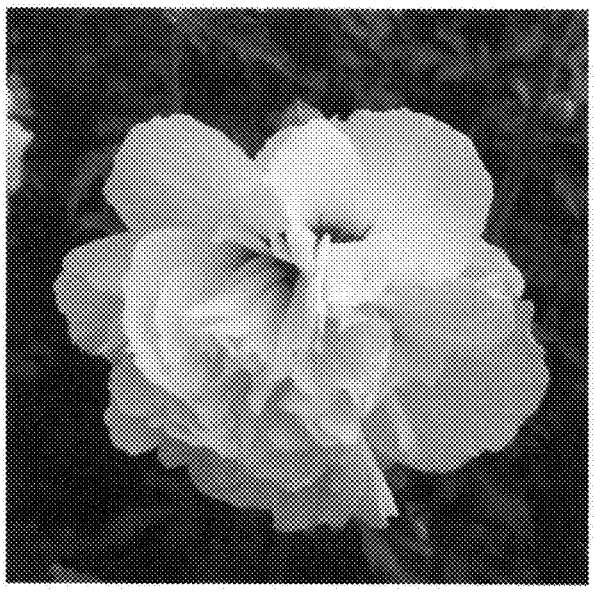

The photograph in FIG. 2 provides a close-up view of the flowers and flower buds of 'MINDOUB1'.

Figure 3:
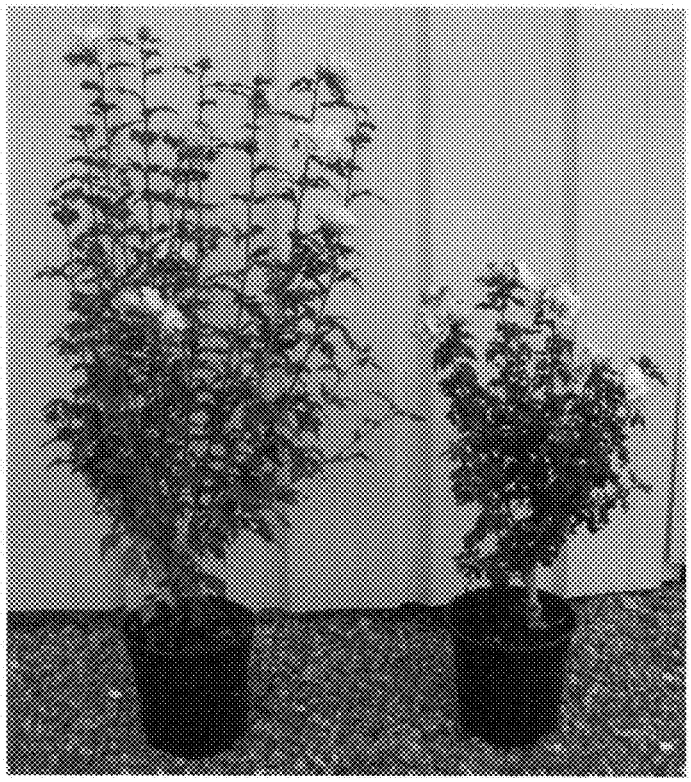

The photograph in FIG. 3 was taken of plants three year in age as grown outdoors in four-gallon containers in LA MENITRE, France and shows a comparison between a flower of 'MINDOUB1' on the left and a flower of 'Leopoldii' on the right.

The colors in the photographs are as close as possible with the digital photography and printing techniques utilized and the color codes in the detailed botanical description accurately describe the new *Hibiscus*.

DETAILED BOTANICAL DESCRIPTION OF THE PLANT

The following is a detailed description of 2.5 year-old plants (from a cutting) of the new cultivar as grown in two-gallon containers in a greenhouse and outdoors in St Paul, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*looming period*.—8 weeks in mid to late summer in LA MENITRE, France.

*Plant type*.—Deciduous shrub.

*Plant habit*.—Upright.

*Height and spread*.—Reaches 1.6 m in height and 70 cm in spread.

*Hardiness*.—At least in U.S.D.A. Zones 5 to 9.

*Diseases*.—Not susceptible or resistance to diseases has been observed.

*Root description*.—Fleshy roots (4 mm in diameter), a blend of 138B and 159A in color, fibrous roots from fleshy roots; 164D in color.

*Root development*.—About 33 days to produce a young rooted plant from a graft.

*Propagation*.—Grafting.

*Growth rate*.—Vigorous.

Stem description:

*Shape*.—Slightly oval.

*Stem color*.—New growth; a blend of 156A and 201D lateral and secondary stems), mature wood; 197A with striations and lenticels of 159.

*Stem size*.—Main stem; an average of 10 cm in length and 2.5 cm in width 3 cm from soil level, lateral stems; an average of 40 cm in length and 9 mm in diameter, secondary stems; an average of 18 cm in length and 3 mm in width.

*Stem surface*.—New growth; pubescent, maturing wood; relatively smooth with striations.

*Stem aspect*.—Held upright with secondary stems held about 15° to vertical.

*Stem strength*.—Very strong.

*Branching*.—An average of 1 main stem, 7 lateral stems, and 2 to 3 secondary stems per lateral branch.

*Internode*.—Average of 2.5 cm.

*Lenticels*.—159A in color, an average of 23 per stem section 3 cm in length and 1 cm in width, roughly orbicular in shape, 1.5 cm in length.

Foliage description:

*Leaf shape*.—Ovate to broadly lanceolate overall.

*Leaf division*.—Simple or 3-leaved.

*Leaf base*.—Cuneate.

*Leaf apex*.—Acute.

*Leaf venation*.—Pinnate, color matches leaf coloration.

*Leaf margins*.—Tri-lobed, upper part of all lobes are serrate to crenate with lower part entire.

*Leaf attachment*.—Petiolate.

*Leaf arrangement*.—Alternate.

*Leaf orientation*.—Held downward to slightly downward.

*Leaf aspect*.—Slightly cupped inward to flat.

*Leaf surface*.—Very finely puberulent on upper and lower surface (appears glabrous).

*Leaf color*.—Young and mature leaves; upper surface 147A, lower surface 147B.

*Leaf size*.—Average of 4.5 cm in length and 4 cm in width when 3-leaved and an average of 4 cm in length and 2 cm in width when simple.

*Leaf quantity*.—About 14 leaves per lateral branch 30 cm in length.

*Petioles and petiolules*.—Average of 9 mm in length and 1 mm in diameter, 137B in color, pubescent surface, petiolules; an average of 3 mm in length and 1 mm in width, 137B in color, pubescent surface.

Flower description:

*Inflorescence type*.—Fully double flowers in clusters of 3 to 5 at terminus.

*Inflorescence size*.—With one flower open and 2 buds an average of 5 cm in width and 3.5 cm in height.

*Lastingness of flowers*.—About 5 days, self cleaning.

*Flower size*.—An average of 4.5 cm in depth and 5 cm in diameter.

*Flower fragrance*.—None.

*Flower shape*.—Carnation-like.

*Flower number*.—3 to 5 per lateral stem.

*Flower aspect*.—Upright to outward.

*Flower bud*.—Elliptic-globose in shape, an average of 2 cm in length and 1.7 cm width, 138A in color (sepal portion), apex (petal portion); a blend of 183B and 162C, surface pubescent.

*Flower attachment*.—Peduncle.

*Petal and petaloid number*.—Average of 12 petals and 60 petaloid stamens.

*Petal and petaloid shape*.—Petals; orbicular to broadly oblanceolate to elliptic, petaloid stamen; range from oblong to elliptic to oblanceolate.

*Petal and petaloid stamen color*.—Upper and lower surface when newly opening; a blend of 11C, 155A with some markings of 187B, upper and lower surface when mature; NN155B and flushed in areas with 72B to 72C, basal spot at all stages on both surfaces; 187C with the very base NN155B, upper and lower surface when fading before drop; 158A with basal spot 79A.

*Petal and petaloid stamen surface*.—Both surfaces smooth and dull with petal spot on petals satiny.

*Petal and petaloid stamen margins*.—Entire to very slightly undulate.

*Petal and petaloid stamen apex*.—Both rounded.

*Petal and petaloid stamen base*.—Petals rounded, petaloid stamens cuneate.

*Petal and petaloid stamen size*.—Petals; up to 2.5 cm in length and width, petaloid stamens; range from 1.2 cm in length and 4 mm in width to 2.5 cm in length and 1 cm in width.

*Sepal number*.—5.

*Sepal shape*.—Narrowly ovate.

*Sepal margin*.—Entire.

*Sepal size*.—Average of 1.8 cm in length and 1.8 cm in width (free potion is triangular in shape and 9 mm in length and width.

*Sepal aspect*.—Upright.

*Sepal surface*.—Outer surface puberulent, inner surface glabrous and glossy.

*Sepal apex*.—Apiculate.

*Sepal base*.—Fused, lower ½.

*Sepal color*.—Young and mature outer and inner surface; 138B.

*Calyx*.—Campanulate in shape, average of 1.8 cm in depth and diameter.

*Peduncles*.—An average of 7 cm in length and 3 mm in diameter, strong and stout, held upright to outward from stem, 138B in color, pubescent surface.

*Pedicels*.—Not present, flowers are solitary from peduncles attached to terminus.

*Bracts*.—6 to 8 bracts held close to calyx, linear in shape, apiculate apex, truncate base, average of 1 cm in length and 1 mm in width, a color 138A on inner and outer surface, surface is slightly pubescent on inner and outer surface.

Reproductive organs:

*Gynoecium*.—1 pistil, stigmas; 3, club-shaped, 158A in color, and 1.5 mm in diameter, style arms; N158C in color and 2 mm in length, style; 2 mm in length and 1. mm in width, glabrous and N158C in color, ovary; urn-shaped, 9 mm in length and 5 mm in width, glandular surface, 149D in color.

*Androecium*.—Stamens; none observed, all converted to petaloid stamens.

*Fruit/seeds*.—None observed, flowers are sterile.

It is claimed:

1. A new and distinct cultivar of *Hibiscus* plant named 'MINDOUB1' as herein illustrated and described.

* * * * *